(12) United States Patent
Gürtler et al.

(10) Patent No.: US 6,559,332 B1
(45) Date of Patent: May 6, 2003

(54) PREPARATION OF A STRAIGHT-CHAIN ACRYLONITRILE DIMER

(75) Inventors: Christoph Gürtler, Köln (DE); Gerhard Braun, Köln (DE); Manfred Jautelat, Burscheid (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/568,893

(22) Filed: May 11, 2000

(30) Foreign Application Priority Data

May 18, 1999 (DE) .......................................... 199 22 642

(51) Int. Cl.[7] ............................................ C07C 255/30
(52) U.S. Cl. ........................................................ 558/364
(58) Field of Search .......................................... 558/364

(56) References Cited

U.S. PATENT DOCUMENTS 5,466,858 A   11/1995  Sugise et al. ............... 558/364

OTHER PUBLICATIONS

Journal of Molecular Catalysis (22) (Month Unavailable), 1983, pp. 29–45, D. T. Tsou et al, "Mechanism of Ruthenium–Catalyzed Linear Dimerization of Acrylonitrile: A Deuterium Labelling Study".

"The Merck Index 12th Edition", (month unavailable) 1996, Merck & co., Whitehouse Station N. J. USA XP002147533, Seite 1044, Absatz 6200.

"Sigma Catalogus", (month unavailable) 1996, Sigma XP002147534, Seite 557, Absatz H5501.

Primary Examiner—Sreeni Padmanabhan
Assistant Examiner—Ebenezer Sackey
(74) Attorney, Agent, or Firm—Godfried R. Akorli; Diderico van Eyl

(57) ABSTRACT

The present invention relates to additives for preparing straight-chain or acrylonitrile dimer from acrylonitrile and to a process for preparing straight-chain acrylonitrile dimer from acrylonitrile in the presence of the additives according to the invention.

6 Claims, No Drawings

PREPARATION OF A STRAIGHT-CHAIN ACRYLONITRILE DIMER

BACKGROUND OF THE INVENTION

The present invention relates to additives for preparing a straight-chain acrylonitrile dimer from acrylonitrile and to a process for preparing straight-chain acrylonitrile dimer from acrylonitrile in the presence of the additives according to the invention.

Straight-chain acrylonitrile dimers are important intermediates for preparing rust inhibitors, vulcanization processes and rubber materials. A further important area of use for straight-chain acrylonitrile dimers is the preparation of hexamethylene-diamine, which is very important for the manufacture of nylon 66.

The dimerization of acrylonitrile in the presence of ruthenium catalysts and hydrogen is described in D. T. Tsou et al., J. Mol. Catal. 22(1), 1983, 29–45. However, the presence of hydrogen gives rise to a secondary reaction in which acrylonitrile is hydrogenated to propionitrile, which is formed in major amounts (33 to 45% yield).

The dimerization of acrylonitrile in the presence of ruthenium catalysts without hydrogen atmosphere is described in DE-A-44 31 307. The dimerization is carried out using carboxylic acids as additives to suppress propionitrile formation. However, carboxylic acids have the disadvantage that they react with acrylonitrile to form β-cyanoesters. This reduces the theoretically attainable yield of acrylonitrile dimer. In addition, the removal of β-cyanoesters from the product mixture is only possible in time-consuming procedures. First, the β-cyanoesters have to be thermally cleaved back to the starting components before these can then be removed from the products by distillation.

It is an object of the present invention to provide additives for the dimerization of acrylonitrile which suppress β-cyanoesters formation and enable straight-chain acrylonitrile dimer to be formed with high selectivity. These and other features, aspects, and advantages of the present invention will become better understood with reference to the following description and appended claims.

DESCRIPTION OF THE INVENTION

It has now been found that the above-named object is achieved with additives for preparing straight-chain acrylonitrile dimer from acrylonitrile in the presence of a ruthenium catalyst, in which these additives are (a) aromatic hydroxy compounds bearing at least one alkyloxycarbonyl substituent and at least one further substituent R on the basic aromatic structure or (b) hetaromatic hydroxy compounds bearing at least one alkyloxycarbonyl substituent and at least one further substituent R on the basic hetaromatic structure;
in which each R is a member selected from the group consisting of halogens, cyano groups, amino groups, amido groups, urethane groups, sulphonyl groups, phosphonyl groups, formyl groups, straight-chain or branched $C_1$–$C_{10}$-alkyl groups, $C_1$–$C_{10}$-alkoxy groups, $C_1$–$C_{10}$-alkyloxo groups, $C_1$–$C_{10}$-alkylsulphinyl groups, $C_1$–$C_{10}$-alkylamino groups, $C_1$–$C_{10}$-haloalkyl groups or $C_1$–$C_{10}$-alkyloxycarbonyl groups;
and the hetaromatic hydroxy compound contains a heteroatom that is selected from nitrogen, sulphur and/or oxygen atoms.

The invention provides important benefits. Additives according to the invention, for instance, first improve straight-chain acrylonitrile dimer selectivity and secondly inhibit β-cyanoesters formation completely.

The aromatic hydroxy compounds used are preferably phenol derivatives, hydroxy-naphthalene derivatives or hydroxyanthracene derivatives, particularly preferably phenol derivatives. If phenol derivatives are used as additives according to the invention, the alkoxycarbonyl substituent and/or the substituent R are disposed ortho and/or para relative to the phenolic group.

The hetaromatic hydroxy compounds used are preferably hydroxythiophene derivatives, hydroxyfuran derivatives, hydroxypyrrole derivatives, hydroxypyridine derivatives or hydroxyimidazole derivatives.

In a preferred embodiment of additives according to the invention, the alkyloxy-carbonyl substituent is straight-chain or branched $C_1$–$C_{10}$-alkyloxycarbonyl, particularly preferably methyloxycarbonyl.

R is preferably formyl, straight-chain or branched $C_1$–$C_{10}$-alkyloxo, straight-chain or branched $C_1$–$C_{10}$-alkyloxycarbonyl or straight-chain or branched $C_1$–$C_{10}$-alkyl, and the most preferred substituents R are methyloxycarbonyl, methyl, acetyl and hydroxyl.

The most preferred additives are methyl 2-hydroxybenzoate, methyl 4-hydroxy-benzoate, trimethyl 2-hydroxy-1,3,5-benzenetricarboxylate, methyl 2,4-dihydroxy-3,6-dimethylbenzoate, methyl 5-acetyl-2-hydroxybenzoate or dimethyl 2-hydroxy-1,5-benzenedicarboxylate.

The invention further provides a process for preparing a straight-chain acrylonitrile dimer, which is characterized in that the acrylonitrile is dimerized in the presence of a ruthenium catalyst and in the additional presence of an additive, in which the additive includes (a) aromatic hydroxy compounds bearing at least one alkyloxycarbonyl substituent and at least one further substituent R on the basic aromatic structure; or (b) hetaromatic hydroxy compounds bearing at least one alkyloxycarbonyl substituent and at least one further substituent R on the basic hetaromatic structure in which each R is selected from the following: halogens, cyano groups, amino groups, amido groups, urethane groups, sulphonyl groups, phosphonyl groups, formyl groups, straight-chain or branched $C_1$–$C_{10}$-alkyl groups, $C_1$–$C_{10}$-alkoxy groups, $C_1$–$C_{10}$-alkyloxo groups, $C_1$–$C_{10}$-alkylsulphinyl groups, $C_1$–$C_{10}$-alkylamino groups, $C_1$–$C_{10}$-haloalkyl groups or $C_1$–$C_{10}$-alkyloxycarbonyl groups;
and the hetaromatic hydroxy compound contains a heteroatom that is selected from nitrogen, sulphur and/or oxygen.

In a preferred embodiment of the process of the invention, the additive and the acrylonitrile are used in a molar ratio that ranges from about 0.001:1 to about 5:1, particularly preferably from about 0.005:1 to about 2:1, most preferably from about 0.01:1 to about 0.1:1.

In a preferred embodiment of the process of the invention, the ruthenium catalysts used are ruthenium salts of organic or inorganic acids or ruthenium complexes, particularly preferably ruthenium complexes. Preferred ruthenium salts of inorganic acids are ruthenium chloride, ruthenium bromide, ruthenium iodide, ruthenium nitrate and ruthenium sulphate. Preferred ruthenium salts of organic acids are ruthenium acetate, ruthenium propionate, ruthenium butanoate, ruthenium pentanoate, ruthenium hexanoate, ruthenium stearate, ruthenium naphthenate, ruthenium oxalate and ruthenium succinate. Preferred ruthenium complexes are dichloro-tetraacrylonitrile-ruthenium, dichloro-tris-(triphenylphosphine)-ruthenium, dichloro-tetrakis-(triphenylphos-phine)-ruthenium, tris-(dimethyl sulphoxide)-ruthenium, dichloro-tetrakis-(dimethyl sulphoxide)-ruthenium, dichloro-tetrakis(diphenyl sulphoxide)-ruthenium, dichloro-tetrakis-(diphenyl sulphide)-ruthenium, dibromo-dichloro-tetrakis-(dimethyl sulphoxide)-ruthenium, dichloro-tetrakis(diphenyl sulphoxide)-ruthenium, dichloro-tetrakis-(diphenyl sulphide)-ruthenium, dibromo-tetrakis-(dimethyl sulphoxide)-ruthenium, dichloro-cyclooctadiene-ruthenium, dichloro-1,4-dicyanobutadiene-ruthenium, dichloro-bis-(methyl acetylenedicarboxy-late)-ruthenium, ruthenium bis-acetylacetonate, dichloro-tris(triphenoxyphos-phine)-ruthenium and dichloro-tetrakis-(dipropyl sulphoxide)-ruthenium. The ruthenium catalyst used is most preferably dichloro-tetrakis-(diphenyl sulphoxide)-ruthenium, which is obtainable by reacting dichloro-cyclooctadiene-ruthenium with diphenyl sulphoxide in toluene.

The ruthenium catalyst used for the process of the invention is used in an amount that ranges from about 0.0001 to about 5 mol %, based on the amount of acrylonitrile used. The catalyst is preferably used in an amount that ranges from about 0.001 to about 2.5 mol %, particularly preferably from about 0.05 to about 0.1 mol %.

The linear acrylonitrile dimers preferably obtained through the process of the invention are 1,4-dicyanobutene, 1,4-dicyanobutadiene and adiponitrile.

The process of the invention makes it possible to dimerize acrylonitrile with or without a reaction medium. Preferably, the dimerization is carried out in a reaction medium. The reaction medium for the process of the invention may include nitriles, sulphoxides, ethers, hydrocarbons, halogenated hydrocarbons, amides, esters, ionic liquids or water, or mixtures thereof. The dimerization is preferably carried out in acetonitrile as reaction medium.

The process of the invention can be carried out within a temperature that ranges from about 70° C. to about 220° C. It is preferably carried out within the temperature ranging from about 100° C. to about 200° C., most preferably within the temperature range from about 110° C. to about 180° C.

The reaction pressure for the process of the invention is customarily within the range from about 0.1 bar to about 50 bar. It is preferably carried out within the range from about 1 bar to about 30 bar, particularly preferably from about 5 bar to about 25 bar.

In a preferred embodiment of the process of the invention, acrylonitrile is dimerized in the presence of dichloro-tetrakis-(diphenyl sulphoxide)-ruthenium and in the presence of the additive dimethyl 2-hydroxy-1,5-benzenedicarboxylate, in acetonitrile as a reaction medium.

The invention is further described in the following illustrative examples in which all parts and percentages are by weight unless otherwise indicated.

EXAMPLES

Examples 1 to 11

The examples were carried out with magnetic stirring in a 30 ml autoclave without walls. The catalysts 1 to 11 recited hereinbelow in Table 1 (0.057 mmol; 0.1 mol % based on acrylonitrile) were introduced as initial charge together with the additive dimethyl 2-hydroxy-1,5-benzene-dicarboxylate (479 mg, 2.3 mmol; 4 mol % based on acrylonitrile), acrylonitrile (3.72 ml; 57 mmol) and 10 ml of acetonitrile. The autoclave was evacuated twice and subsequently flooded with nitrogen. The dimerization was carried out at a nitrogen pressure of 20 bar. Example 8 is a comparative example.

TABLE 1

| Example | Catalyst | Reaction time (h) | Yield of linear dimer (%) | Selectivity with regard to linear dimer (%) |
|---|---|---|---|---|
| 1 | $RuCl_2COD$ | 12 | 9 | 82 |
| 2 | $RuCl_2(DMSO)_4$ | 12 | 12 | 82 |
| 3 | $RuCl_2(Dimethyl\ acetylenedicarboxylate)_2$ | 3 | 4 | 72 |
| 4 | $RuCl_2(1,4\ Dicyanobutadiene)$ | 3 | 2 | 68 |
| 5 | $RuCl_2(DPhSO)_4$ | 18 | 13 | 87 |
| 6 | $Ru(acac)_2$ | 3 | 5 | 5 |
| 7 | $RuCl_2[P(OPh3)]_3$ | 12 | 4 | 87 |
| 8 | $OsCl_2(DMSO)_4$ | | 0 | — |
| 9 | $RuBr_2(DMSO)_4$ | 12 | 4 | 73 |
| 10 | $RuCl_2(DPrSO)_4$ | 12 | 6 | 79 |
| 11 | $RuCl_2(Diphenyl\ sulphide)_4$ | 12 | 10 | 81 |

COD = cyclooctadiene, DMSO = dimethyl sulphoxide, DPhSO = diphenyl sulphoxide, acac = acetylacetonate, Ph = phenyl, Pr = propyl.

Preparation of dichloro-tetrakis-(diphenyl sulphoxide)-ruthenium

A 10 ml Schlenk tube was charged with 3.5 ml of devolatilized toluene, and 292 mg $RuCl_2COD$ were dissolved therein. 805 mg of diphenyl sulphoxide were added to the solution, and the mixture was stirred at 100° C. for 1 h. After the reaction had ended, the mixture was slowly cooled down. To crystallize the reaction product, the reaction solution was allowed to stand at 4° C. under argon for 12 h. The resultant precipitate was switched off with suction, washed with petroleum ether and dried under a high vacuum. The yield was 28% of theory.

Examples 12 to 20

The examples were carried out with magnetic stirring in a 30 ml autoclave without walls. The catalyst dichloro-tetrakis-(diphenyl sulphoxide)-ruthenium (56 mg; 0.057 mmol; 0.1 mol % based on acrylonitrile) was introduced as initial charge together with the additives 12 to 20 reported in Table 2 (4 mol % based on acrylonitrile), acrylonitrile (3.72 ml; 57 mmol) and 10 ml of acetonitrile. The autoclave was evacuated twice and subsequently flooded with nitrogen. The dimerization was carried out at a nitrogen pressure of 20 bar. Examples 12 to 14 are comparative runs.

TABLE 2

| Example | Additive | Reaction time (h) | Yield of linear dimer (%) | Selectivity with regard to linear dimer (%) |
|---|---|---|---|---|
| 12 | $CH_3(CH_2)_2PO_4H(CH_2)_2CH_3$ | 12 | 0 | — |
| 13 | 2-Hydroxybenzonitrile | 3 | 0 | — |
| 14 | 2-Acetamidophenol | 3 | 0 | — |
| 15 | Methyl 2-hydroxybenzoate | 12 | 9 | 55 |
| 16 | Methyl 4-hydroxybenzoate | 12 | 8 | 50 |
| 17 | Trimethyl 2-hydroxy-1,3,5-benzenetricarboxylate | 12 | 8 | 42 |
| 18 | Methyl 2,4-dihydroxy-3,6-dimethylbenzoate | 12 | 5 | 69 |
| 19 | Methyl 5-acetyl-2-hydroxy-benzoate | 3 | 8 | 78 |
| 20 | Dimethyl 2-hydroxy-1,5-benzenedicarboxylate | 18 | 12 | 92 |

Although the present invention has been described in detail with reference to certain preferred versions thereof, other variations are possible. Therefore, the spirit and scope of the appended claims should not be limited to the description of the versions contained therein.

What is claimed is:

1. A process for preparing a straight-chain acrylonitrile dimer comprising the step of dimerizing an acrylonitrile in the presence of a ruthenium catalyst and in the presence of an additive that is:

(a) an aromatic hydroxy compound having a basic aromatic structure and bearing at least one alkyloxycarbonyl substituent and at least one further substituent R on the basic aromatic structure, or (b) a hetaromatic hydroxy compound having a basic heteroaromatic structure and bearing at least one alkyloxycarbonyl substituent and at least one further substituent R on the basic hetaromatic structure;

wherein each R is a member selected from the group consisting of a halogen, a cyano group, a amino group, an amido group, a urethane group, a sulphonyl group, a phosphonyl group, a formyl group, a straight-chain $C_1$–$C_{10}$-alkyl group, a branched $C_1$–$C_{10}$-alkyl group, a $C_1$–$C_{10}$-alkoxy group, a $C_1$–$C_{10}$-alkyloxo group, a $C_1$–$C_{10}$-alkylsulphinyl group, a $C_1$–$C_{10}$-alkylamino group, a $C_1$–$C_{10}$-haloalkyl group, and a $C_1$–$C_{10}$-alkyloxycarbonyl group; and wherein each hetaromatic hydroxy compound contains a heteroatom selected from the group consisting of nitrogen, sulphur and oxygen.

2. The process of claim 1, wherein the additive is used in an amount ranging from about 0.001 to about 2 times the molar amount of acrylonitrile used.

3. The process of claim 1, wherein the ruthenium catalysts used are selected from the group consisting of organic ruthenium salts, inorganic ruthenium salts and ruthenium complexes.

4. The process of claim 1, wherein the ruthenium catalyst used is selected from the group consisting of dichloro-tetrakis (dimethyl sulphoxide)-ruthenium, dichloro-tetrakis-(diphenyl sulphoxide)-ruthenium, dichloro-tetrakis-(diphenyl sulphide)-ruthenium, dibromo-tetrakis-(dimethyl sulphoxide)-ruthenium, dichloro-cyclooctadiene-ruthenium, dichloro-1,4dicyanobutadiene-ruthenium, dichloro-bis-(methyl acetylenedicarboxylate)-ruthenium, ruthenium bis-acetylacetonate, dichloro-tris-(triphenoxy-phosphine)-ruthenium and dichloro-tetrakis-(dipropyl sulphoxide)-ruthenium catalysts.

5. The process of claim 1, wherein the catalyst is used in an amount that ranges from about 0.001 to about 5 mol %, based on the molar amount of acrylonitrile used.

6. The process of claim 1, wherein the dimerization is carried out in a reaction medium which includes at least one compound selected from the group consisting of nitritles, sulphoxides, ethers, hydrocarbons, halogenated hydrocarbons, amides, esters and water.

* * * * *